United States Patent
Luu et al.

(10) Patent No.: US 7,521,404 B2
(45) Date of Patent: Apr. 21, 2009

(54) ANTIMICROBIAL LIQUID HAND SOAP COMPOSITION WITH TACTILE SIGNAL COMPRISING A PHOSPHOLIPID SURFACTANT

(75) Inventors: Phuong V. Luu, Appleton, WI (US);
Kurt K. Konietzki, Neenah, WI (US);
David W. White, Clintonville, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 0 days.

(21) Appl. No.: 11/304,353

(22) Filed: Dec. 15, 2005

(65) Prior Publication Data

US 2006/0135384 A1 Jun. 22, 2006

Related U.S. Application Data

(60) Provisional application No. 60/637,101, filed on Dec. 16, 2004.

(51) Int. Cl.
*C11D 3/36* (2006.01)
*C11D 3/48* (2006.01)
*C11D 1/37* (2006.01)

(52) U.S. Cl. .................. 510/131; 510/138; 510/130; 510/149; 510/150; 510/155; 510/156; 510/319; 510/351; 510/352; 510/357; 510/382; 510/388; 510/423; 510/428; 510/431; 510/436; 510/468

(58) Field of Classification Search ................. 510/138, 510/130, 131, 149, 150, 155, 156, 319, 351, 510/352, 357, 382, 388, 423, 428, 431, 436, 510/468
See application file for complete search history.

(56) References Cited

U.S. PATENT DOCUMENTS

| | | | | |
|---|---|---|---|---|
| 4,753,749 A | | 6/1988 | McIntosh | 510/382 |
| 5,635,462 A | * | 6/1997 | Fendler et al. | 510/131 |
| 5,635,469 A | * | 6/1997 | Fowler et al. | 510/406 |
| 5,683,683 A | * | 11/1997 | Scafidi | 424/70.19 |
| 5,688,752 A | | 11/1997 | Turner | 510/159 |
| 5,709,872 A | * | 1/1998 | Van Rees | 424/420 |
| 5,781,942 A | | 7/1998 | Allen et al. | 4/623 |
| 5,804,203 A | * | 9/1998 | Hahn et al. | 424/401 |
| 5,945,910 A | | 8/1999 | Gorra | 340/573.1 |
| 6,022,551 A | * | 2/2000 | Jampani et al. | 424/405 |
| 6,296,880 B1 | * | 10/2001 | Murad | 424/616 |
| 6,331,293 B1 | | 12/2001 | Smith et al. | 424/59 |
| 6,383,523 B1 | * | 5/2002 | Murad | 424/616 |
| 6,451,775 B1 | | 9/2002 | Smith et al. | 514/77 |
| 6,613,755 B2 | | 9/2003 | Peterson et al. | 514/63 |
| 2002/0002124 A1 | | 1/2002 | Biedermann et al. | 510/218 |
| 2002/0012648 A1 | | 1/2002 | Orthoefer | 424/70.27 |
| 2002/0022660 A1 | * | 2/2002 | Jampani et al. | 514/635 |
| 2002/0061500 A1 | | 5/2002 | Collopy | 434/238 |
| 2002/0103092 A1 | | 8/2002 | Tashjian et al. | 510/130 |
| 2002/0141959 A1 | | 10/2002 | Peterson et al. | 424/70.12 |
| 2003/0031727 A1 | * | 2/2003 | Hahn et al. | 424/617 |
| 2005/0101515 A1 | * | 5/2005 | Pawson et al. | 510/512 |

OTHER PUBLICATIONS

Colonial Chemical, Inc. product bulletin entitled "Colalipid Products", pp. 1-5, revised Feb. 13, 2003.

* cited by examiner

*Primary Examiner*—Charles I Boyer
(74) *Attorney, Agent, or Firm*—Michael W. Ferrell

(57) ABSTRACT

An antimicrobial liquid hand soap composition includes: (a) water; (b) a primary hand soap composition; (c) a biocide; and (d) a glutinous surfactant having a relative contact angle value with water of at least about +10° with respect to the primary hand soap composition. The glutinous surfactant is present in an amount effective to alter the tactile properties of the primary soap composition to promote longer and more thorough hand washing by eliciting a response to the soap's feel on the skin.

24 Claims, No Drawings

ANTIMICROBIAL LIQUID HAND SOAP COMPOSITION WITH TACTILE SIGNAL COMPRISING A PHOSPHOLIPID SURFACTANT

CLAIM FOR PRIORITY

This non-provisional application claims the benefit of the filing date of U.S. Provisional Patent Application Ser. No. 60/637,101, of the same title, filed Dec. 16, 2004. The priority of U.S. Provisional Patent Application Ser. No. 60/637,101 is hereby claimed and the disclosure thereof is incorporated into this application by reference.

TECHNICAL FIELD

The present invention relates generally to liquid hand soap compositions and in a preferred embodiment to a liquid soap including at least two anionic surfactants and a glutinous additive such as a cationic phospholipid surfactant having a relative contact angle value with water of at least about +10° with respect to other ingredients. The phospholipids act as a tactile signal; promoting more thorough hand cleansing.

BACKGROUND OF THE INVENTION

Media attention to cases of food poisoning, strep infections, and the like due to microbial contamination has increased public awareness of the dangers posed by inadequate hygiene, particularly in the food service and health industries. Bacteria found on the skin can be divided into two groups: resident and transient bacteria. Resident bacteria are Gram positive bacteria which are established as permanent microcolonies on the surface and outermost layers of the skin and play an important, helpful role in preventing the colonization of other, more harmful bacteria and fungi. Transient bacteria are bacteria which are not part of the normal resident flora of the skin, but can be deposited when airborne contaminated material lands on the skin or when contaminated material is brought into physical contact with it. Transient bacteria are also typically divided into Gram positive and Gram negative subclasses. Gram positive bacteria include pathogens such as *Staphylococcus aureus, Streptococcus pyogenes* and *Clostridium botulinum*. Gram negative bacteria include pathogens such as *Salmonella, Escherichia coli, Klebsiella, Haemophilus, Pseudomonas aeruginosa, Proteus* and *Shigella dysenteriae*. Gram negative bacteria are generally distinguished from Gram positive by an additional protective cell membrane which generally results in the Gram negative bacteria being less susceptible to topical antibacterial actives. The American Society of Microbiologists has indicated that adequate hand washing will greatly reduce the incidence of communicable diseases.

Many soap formulations have been developed which have an antimicrobial agent such as a suitable phenol as well as emollients. It is desirable that the hand washing formulation not only remove bacteria from the hands, but also leave behind an antibacterial protective layer that also softens and conditions.

United States Patent Application 2002/0141959 and U.S. Pat. No. 6,613,755, both to Peterson et al., disclose antimicrobial skin preparations containing organosilane quaternary compounds that remain on the skin, are substantive to it and reduce or eliminate bacteria, viruses and fungi present and prevent future contamination by their presence. Antimicrobial skin compositions are also disclosed in published United States Patent Application No. 2002/0103092, to Tashjian et al., which contain an anionic surfactant, an amphoteric surfactant, a cationic conditioning agent, an antibacterial agent and water.

High phospholipid-containing dermatological compositions are disclosed in United States Patent Application No. 2002/0012648 to Orthoefer. The relatively high concentration of phospholipids impart a thin macromolecular layer to the skin, which permits natural hydration while providing antioxidant and natural sun-blocking effects. Typical structures of these phospholipids are shown below in structure 1:

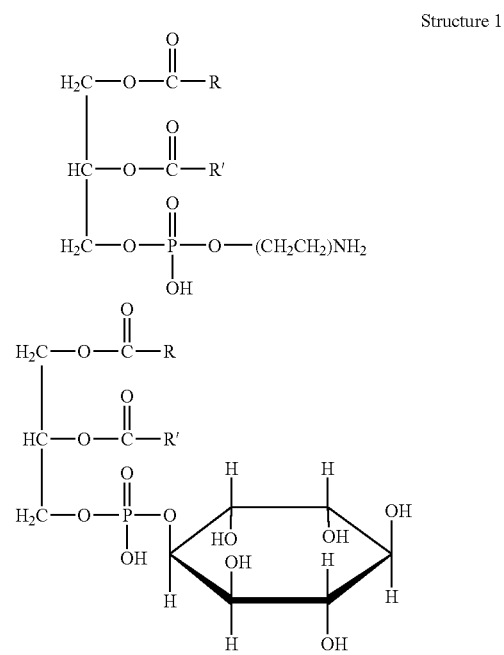

Structure 1 where R and R' are fatty acids having the formula $CH_3(CH_2)_n COO$, with n equal to between about 4 and 22.

Phospholipids are also present in antimicrobial cleansing compositions described in United States Patent Application No. 2002/0002124 to Biedermann et al. The compositions are mild to the skin and provide improved antimicrobial protection. U.S. Pat. No. 6,451,775 to Smith et al. discloses novel castor oil amidopropyl dimethyl phospholipids as emulsifiers that are substantive to the skin and are well tolerated by human tissue:

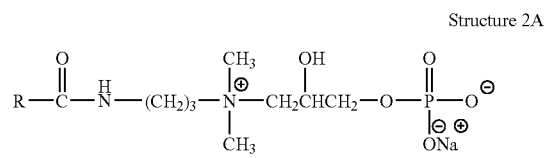

Structure 2A where R represents the ricinoleic moiety:

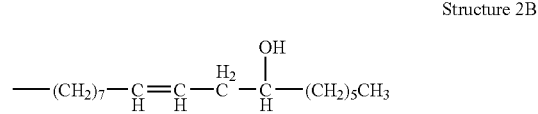

Structure 2B

A Colonial Chemical product bulletin (Feb. 13, 2003) discloses an antimicrobial hand cleanser containing 87% water, 8.5% disodium oleamido MEA sulfosuccinate, 2.5% cocamidopropyl phoshatidyl PG-dimonium chloride (Colalipid™ C) and 0.4% chlorhexidine gluconate as a biocide. That same bulletin describes Colalipid™ surfactants as unregistered antimicrobials and notes a frequent use hand soap composition with 2% Colalipid™ C.

U.S. Pat. No. 6,331,293, also to Smith et al. also discloses phospholipids:

equate hygiene. A number systems and devices to encourage longer and more thorough handwashing have accordingly been developed.

Collopy in United States Patent Application 2002/0061500 discloses a hand-washing device containing a display panel that encourages the user to wash their hands for about 15 seconds to remove germs. Gorra, U.S. Pat. No. 5,945,910 discloses method and apparatus for monitoring and reporting hand washing, which includes a sensor for signaling the dispensation of a cleaning agent from a dispenser, and a report-

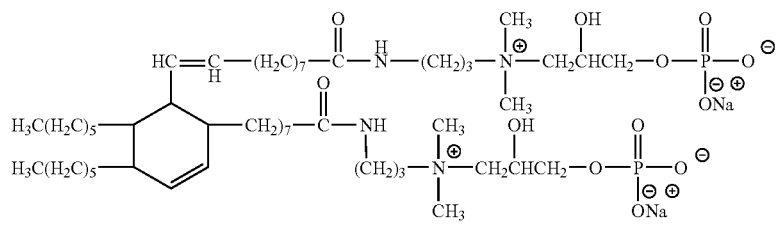

Structure 3

U.S. Pat. No. 5,688,752, to Turner, describes various lipids for cleansing compositions that prevent or ameliorate skin dryness, skin wrinkling, chapping or ageing. Quaternized phosphate esters are included as ingredients in dry wash compositions that impart conditioning properties to the skin, as described in U.S. Pat. No. 5,683,683 to Scafidi. Phospholipids are used as "primary surfactants" in antimicrobial cleansing compositions described in U.S. Pat. No. 5,635,462 to Fendler et al. They are used to act upon or in conjunction with a substituted phenol to further enhance its antimicrobial activity. U.S. Pat. No. 4,753,749, to McIntosh, discloses microbiocidal cleaning agents containing amine alkyl phosphate additives as the active ingredients:

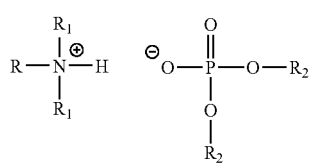

Structure 4 where:
R=an alkyl group containing 1 to 24 carbon atoms;
$R_1$=an alkyl group containing from 1 to 3 carbon atoms; and
$R_2$=an alkyl group containing from 1 to 5 carbon atoms.

In the preferred structure, R equals $C_{12}H_{25}$, $R_1$ equals $CH_3$ and $R_2$ equals $C_2H_5$.

Washing of the skin, especially the hands, with antimicrobial soap formulations can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria. Recent surveys, however, have revealed that while nearly 95% of people claim to have washed their hands after use of public restrooms, actual observations reveal that this figure does not exceed about 66%. Notwithstanding increased awareness, there is a tendency to rush the hand washing process which leads to inading and monitoring module. Allen et al. U.S. Pat. No. 5,781,942 discloses wash stations and method of operation, which monitors hand washing and assists in hand washing. These systems are relatively expensive and difficult to implement; oftentimes involving training and monitoring personnel. Even when such steps have been taken, there is little certainty that all personnel have followed proper washing procedures.

SUMMARY OF THE INVENTION

It has been found in accordance with the invention that adding a surfactant having glutinous (somewhat oily yet somewhat unctuous as well) tactile properties to conventional hand soap formulations promotes longer hand washing and rinsing times leading to better hygiene, without complex hardware and software and without substantial implementation expense. There is thus provided in one aspect of the invention an antimicrobial liquid hand cleanser composition comprising: (a) water; (b) a primary hand cleanser surfactant composition, including a biocide; and (c) a glutinous surfactant component having a relative contact angle value with water of at least about +10 degrees with respect to the primary hand cleanser surfactant composition, the glutinous surfactant being present in an amount effective to alter the tactile properties of the primary cleanser surfactant composition, with the proviso that the glutinous surfactant is present in an amount of less than about 20 weight % based on the combined dry weight of the primary hand cleanser surfactant composition and the glutinous surfactant. In a series of preferred embodiments, the glutinous surfactant component is preferably selected from the group consisting of: cocamidopropyl PG-dimonium chloride phosphate; dimer dilinoleamido-propyl PG-dimonium chloride phosphate; sodiumgrapeseedamidopropyl PG-dimonium chloride phosphate; sodium olivamidopropyl PG-dimonium chloride phosphate; linoleamidopropyl PG-dimonium chloride phosphate; PEG-8 dimethicone sunfloweramidopropyl PG-dimonium complex; sunfloweramidopropyl phosphate PG-dimonium chloride and mixtures thereof.

Preferably, the glutinous surfactant component has a relative contact angle value with water of at least about +20° with respect to the primary soap composition; while in most cases the glutinous surfactant is present in an amount of from about 1% to about 10% based on the total (wet) weight of the composition. In particularly preferred cases, the glutinous surfactant is present in an amount of from about 3% to about 7% based on the total weight of the composition and the primary soap composition comprises at least two anionic surfactants. Optionally, the primary soap composition includes at least one nonionic surfactant.

While any suitable biocide may be used, preferred are those which include halogenated aromatic compounds. One preferred ingredient, for example, is:

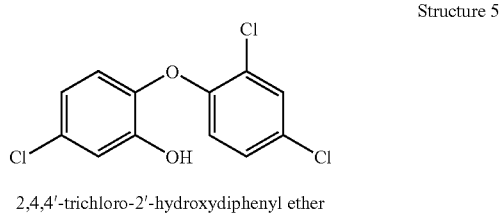

Structure 5

2,4,4'-trichloro-2'-hydroxydiphenyl ether

A chelating agent such as EDTA or the like is optionally provided along with glycerine or other conventional components for liquid soaps.

Another antimicrobial liquid hand cleanser composition of the invention includes: (a) up to about 75% by weight water; (b) a primary hand cleanser surfactant composition, including a biocide; and (c) a glutinous surfactant component having a relative contact angle value with water of at least about +10° with respect to the primary hand cleanser surfactant composition, the glutinous surfactant being present in an amount effective to alter the tactile properties of the primary cleanser surfactant composition.

Still yet another embodiment of the invention is an antimicrobial liquid hand cleanser composition comprising: (a) water; (b) a primary hand cleanser surfactant composition; and (c) a glutinous surfactant component having a relative contact angle value with water of at least about +10° with respect to the primary hand cleanser surfactant composition, the glutinous surfactant being present in an amount effective to alter the tactile properties of the primary cleanser surfactant composition, with the proviso that the glutinous surfactant is present in an amount of at least about 3% by weight and up to about 10% by weight based on the weight of the composition including water.

There is provided in still yet a further aspect of the invention an antimicrobial liquid hand cleanser composition comprising: (a) water present in an amount of up to about 75% by weight; (b) a primary hand cleanser surfactant composition; and (c) a glutinous surfactant present in an amount of at least about 3% by weight and up to about 10% by weight based on the weight of the composition including water, the glutinous surfactant being operative to increase rinse time with respect to a like composition consisting of water and the primary cleanser surfactant composition. Preferably, the glutinous surfactant is operative to increase rinse time at least 10% with respect to a like composition consisting of and the primary soap composition; 15 or 20 percent increases in rinse time are preferred.

The inventive compositions are typically made by preparing a mixture of: (a) water in an amount of up to about 75% by weight of the composition; (b) a primary hand cleanser surfactant composition; and (c) a glutinous surfactant wherein the glutinous surfactant is present in an amount of at least about 3% by weight and up to about 10% by weight based on the weight of the composition including water and wherein the glutinous surfactant alters the tactile properties of the composition so as to lengthen hand cleansing times.

Still yet other advantages of the invention will become apparent from the discussion which follows.

DETAILED DESCRIPTION OF THE INVENTION

The invention is described in detail below for purposes of illustration, only. Modifications within the spirit and scope of the invention, set forth in the appended claims, will be readily apparent to one of skill in the art.

As used herein, terminology is given its ordinary meaning as supplemented below.

"Biocide" and the like terminology means and includes any substance that kills or inhibits the growth of microorganisms such as bacteria, viruses, molds, slimes, fungi, etc. Biocidal chemicals include halogenated aromatics, chlorinated hydrocarbons, organometallics, metallic salts, organic sulfur compounds, quaternary ammonium compounds, phenolics and the like.

"Like composition" refers to a composition which is substantially identical except that a specified component has been replaced with water, alcohol, polyol or mixture of such substitute components.

"Primary hand cleanser surfactant composition" refers to the collective ingredients of a surfactant composition of the invention exclusive of the glutinous surfactant component; optionally including a biocide. The primary surfactant formulation may be referred to on either a wet or dry basis. The primary hand cleanser surfactant composition typically includes one or more surfactants as the primary surfactants of the composition as well as preservatives, fragrances and so forth. The primary hand cleanser surfactant composition may contain anionic surfactants, cationic surfactants, nonionic surfactants and so forth. Examples of suitable conventional anionic surfactants generally include, but are not necessarily limited to, fatty acid soaps as well as sulfates, carboyxlates, sulfonates, sulfosuccinates, phosphonates, phosphates, sarcosinates and isethionates of hydrophobic moieties. Other suitable surfactants for the primary hand cleanser surfactant composition are surfactants selected from the group consisting of amine oxides, phospholipids, partially neutralized carboxylic acids and diacids, betaines, ethoxylated methylglucosides and mixtures thereof. The amount of primary surfactant(s) to be added to the composition of the present invention is somewhat dependent upon the number of primary surfactants added. However, the amount of all of the primary surfactants together generally will not exceed more than about 20-25% by weight of the composition including water.

"Primary surfactant" means a surfactant included in the primary hand soap composition.

"Glutinous surfactant composition" means one or more surfactants added to the primary hand soap composition in order to alter its tactile properties. Some preferred surfactants are available from Colonial Chemical and are listed below in Table 1.

TABLE 1

Glutinous Phospholipids

| COLALIPID ™ | Chemical Description | Oil Source | Primary R-Group |
|---|---|---|---|
| C | Cocamidopropyl PG-Dimonium Chloride Phosphate | Coconut | Cocamidopropyl |
| SAFL | Linoleamidopropyl PG-Dimonium Chloride Phosphate | Safflower | Linoleamidopropyl |
| SUN | Sunfloweramidopropyl Phosphate PG-Dimonium Chloride | Sunflower | Linoleamidopropyl |
| OL | Sodium Olivamidopropyl PG-Dimonium Chloride Phosphate | Olive | Oleamidopropyl |
| DLO | Dimer Dilinoleamidopropyl PG-Dimonium Chloride Phosphate | Dimer Acd | Di-Linoleamidopropyl |
| SIL | PEG-8 Dimethicone Sunfloweramidopropyl PG-Dimonium Complex | Sunflower | Silicone and Linoleamidopropyl |
| GS | Sodiumgrapeseedamidopropyl PG-Dimonium Chloride Phosphate | Grapeseed | Linoleamidopropyl |

Further details may be seen in U.S. Pat. No. 6,331,293 to Smith et al.

The composition may also include other additives such as thickeners, emollients, chelating and sequestering agents, fragrances, coloring agents, opacifying agents, pearlizing agents, vitamins and the like. For example, the composition may include a polymer viscosifier or thickener such as hydroxyethyl cellulose to make the composition more aesthetically pleasing. Examples of other suitable polymer viscosifiers include, but are not necessarily limited to, hydroxypropyl cellulose, methylcellulose, and carboxymethyl cellulose. Examples of suitable chelating agents for the present invention are ethylenediaminetetra-acetic acid (EDTA), and its salts such as tetra sodium EDTA. An example of a particular pearlizing agent is ethylene glycol distearate. Generally, these additives are used in amounts, which do not affect the essential nature of the composition with respect to its antimicrobial properties.

The angle defined between a tangent to a liquid droplet surface at its air/liquid interface at the droplet's line of contact with a solid and the solid substrate surface upon which the droplet rests (as measured through the liquid) is generally referred to as the contact angle of a liquid with a solid. The contact angle may be measured at any point at the line of contact of the three phases, air/liquid/solid. "Contact angles" herein refer to contact angles of coated paperboard with water at room temperature as measured with a goniometer. Inasmuch as contact angles decayed over time, the contact angle for purposes of determining relative contact angle with respect to reference compositions is taken at 1 second of contact time, preferably averaged over at least 5 trials.

The relative contact angle value with water with respect to a control composition is calculated as the difference between the measured contact angles with water of the test composition and the control composition at 1 second. Details appear in connection with Table 4.

EXAMPLES

Test composition A was prepared by blending water and the ingredients listed in Table 2 to produce an antimicrobial hand soap composition having the relative amounts shown.

TABLE 2

Hand Soap Formulation A

| Formula Raw Material Ingredient | | Standard Formula (%/W) | | | Raw Material Supplier (Manufacturer) | Manufacturer's Trade Name |
|---|---|---|---|---|---|---|
| | | Target % | Min % | Max % | | |
| Water | Water | 49.982000 | — | — | Chester | — |
| Sulfochem B-D37K | Ammonium Laurel Sulfate (and) Sodium Laureth Sulfate (and) Cocamidopropyl Betaine (and) Cocamide MEA (and) PEG-150 Distearate | 45.000000 | — | — | Chemron | Sulfochem B-D37K |
| Glycerin | Glycerin | 2.000000 | — | — | Harris &Ford [Vopak(VWR)] | Glycerin |
| D-R Sulfosuccinate (39%) | Disodium Ricinoleamido MEA-Sulfosuccinate | 1.000000 | | | Harcros Chemicals | Mackanate RM |

TABLE 2-continued

Hand Soap Formulation A

| Formula Raw Material Ingredient | | Standard Formula (%/W) | | | Raw Material Supplier (Manufacturer) | Manufacturer's Trade Name |
|---|---|---|---|---|---|---|
| | | Target % | Min % | Max % | | |
| Isostearamidopropyl Morpholine Lactate | Isostearamidopropyl Morpholine Lactate | 0.500000 | | | Harcros Chemicals | Mackanate 426 |
| DMDM Hydantoin | DMDM Hydantoin | 0.400000 | | | Harcros (McIntyre)[Lonza] | Glydant (DMDM Hyantoin) |
| Triclosan | Triclosan | 0.300000 | | | Ciba/Glopaak/Lexichem | 2,4,4-Trichloro-2-hydroxydiphenyl Ether |
| Ammonium Chloride | Ammonium Chloride | 0.300000 | 0.2 | 0.5 | Vopak (VWR) | Ammonium Chloride |
| Citric Acid | Citric Acid | 0.008000 | 0.005 | 0.02 | Vopak(Ashland Chemical Co.) | Citric Acid Anhyd, USP/FCC |
| Versene 100 (Chelating Agent) | Tetrasodium EDTA | 0.100000 | — | — | Noveon (Ashland Chemical) | Versene 100 |
| Violet #2 (0.5%) | Ext. D&C Violet #2 | 0.096000 | — | — | Noveon(Pylam Products) | Ext. D&C Violet #2 |
| Red #4 (1%) | FD&C Red #4 | 0.014000 | — | — | Noveon(Pylam Products) | FD&C Red #4 |
| Fragrance | Fragrance | 0.300000 | — | — | Givaudan | TG040027/A |

The primary surfactant composition of Formulation A appears in Table 3.

TABLE 3

Primary Surfactant Composition

| | Weight Percent Range | |
|---|---|---|
| Component | Minimum | Maximum |
| Ammonium Lauryl Sulfate | 12 | 16 |
| Sodium Laureth Sulfate | 9 | 12 |
| Cocamide MEA | 1 | 3.0 |
| Cocamidopropyl Betaine | 4 | 7.0 |
| PEG-150 Disearate | — | 1.0 |

A hydrophobic coated paperboard substrate was used to evaluate the relative contact angles of Hand Soap Formulation A, the various glutinous surfactants referred to above, as well as compositions of the invention which include a glutinous surfactant component in addition to the primary hand soap composition of Formulation A. To this end, a series of formulations were overcoated onto the paperboard substrate using a coil coating rod (#7); the films applied had a weight of about 8 g/m², dry basis. A water droplet (0.01 ml) was placed on a dried film and contact angle over time measured with a Ramé-Hart Goniometer (Model #100-00115, equipped with a video camera, zoom lens and green light). All testing was at room temperature (approximately 20° C.) and films were dried for twenty-four hours prior to testing under ambient conditions. Inasmuch as contact angle decays rapidly in many cases, it is important that the instrument used is capable of measuring the angle accurately with respect to time. Note that particularly preferred surfactants such as Colalipid™ C and Colalipid™ C DLO exhibit relatively stable contact angle values by this method.

The relative contact angle value is calculated by subtracting the contact angle at 1 second of the control from the contact angle at 1 second from the test composition.

Results appear in Tables 4 and 5 below.

TABLE 4

WATER CONTACT ANGLE vs. TIME

| | | Water Contact Angle (Degree) | | | | |
|---|---|---|---|---|---|---|
| Example # | References | 1 Sec. | 5 Sec. | 10 Sec. | 20 Sec. | 40 Sec. |
| 1 | Control - Paper Board Non-treated | 98 | 96 | 93 | 90 | 86 |
| 2 | Formulation A | 29 | 0 | 0 | 0 | 0 |
| 3 | Colalipid ™ C | 64 | 62 | 55 | 36 | 0 |
| 4 | Colalipid ™ DLO | 91 | 71 | 62 | 55 | 47 |
| 5 | Colalipid ™ GS | 50 | 27 | 0 | 0 | 0 |
| 6 | Colalipid ™ OL | 59 | 40 | 35 | 0 | 0 |
| 7 | Colalipid ™ SAFL | 48 | 25 | 0 | 0 | 0 |
| 8 | Colalipid ™ SIL | 39 | 0 | 0 | 0 | 0 |
| 9 | Colalipid ™ SUN | 52 | 27 | 0 | 0 | 0 |
| 10 | Formulation A/5% Colalipid ™ C | 38 | 14 | 0 | 0 | 0 |
| 11 | Formulation A/5% Colalipid ™ DLO | 38 | 0 | 0 | 0 | 0 |
| 12 | Formulation A/5% Colalipid ™ GS | 37 | 0 | 0 | 0 | 0 |
| 13 | Formulation A/5% Colalipid ™ OL | 38 | 0 | 0 | 0 | 0 |
| 14 | Formulation A/5% Colalipid ™ SAFL | 36 | 0 | 0 | 0 | 0 |
| 15 | Formulation A/5% Colalipid ™ SIL | 38 | 0 | 0 | 0 | 0 |
| 16 | Formulation A/5% Colalipid ™ SUN | 34 | 0 | 0 | 0 | 0 |

In Examples 10-16, water in Formulation A was replaced with the specified surfactant. The only difference between Formulation A and Examples 10-16 on a dry basis is thus phospholipids content.

TABLE 5

Relative Contact Angle Values with Respect to Formulation A

| Example | Surfactant | Relative Contact Angle Values |
|---|---|---|
| 3 | Colalipid ™ C | +35 |
| 4 | Colalipid ™ DLO | +62 |
| 5 | Colalipid ™ GS | +21 |
| 6 | Colalipid ™ OL | +30 |
| 7 | Colalipid ™ SAFL | +19 |
| 8 | Colalipid ™ SIL | +10 |
| 9 | Colalipid ™ SUN | +23 |

The data of Tables 4 and 5 are surprising when one considers that the various surfactants tested have relatively high HLB values; see Table 6.

TABLE 6

HLB Values for Selected Phospholipds

| COLALIPID ™ C (coconut oil phospholipid) | HLB 17-19 |
|---|---|
| COLALIPID ™ SAFL (linoleyl phospholipid) | HLB 17-19 |

Without intending to be bound by any theory, it is believed that the glutinous and ointment-like nature of the phospholipids increases contact angles of soap compositions despite the relatively high HLB values of the surfactants.

Even more surprising is the effect that these high HLB value surfactants have on cleansing times observed in panel testing, discussed below.

Twenty (20) female test panelists were recruited for purposes of testing the effect of the tactile-modifying component on hand washing time. The panelists were prompted to wash their hands normally including generally the steps of:

(1) adjusting the running water temperature until they felt comfortable;
(2) wetting their hands with warm water;
(3) applying about 2 grams of soap on a their wet hands;
(4) rubbing their hands with soap without running water;
(5) rinsing their hands with warm running water; and
(6) drying their hands with a paper towel.

Half of the panelists tested the control soap of Formulation A first, then the same soap with 5% Colalipid™ C (Example 10), while the order was reversed for the other 10 panelists.

The time from starting step (4) to the end of step (6) was recorded as the wash/rinse/drying time; the time from starting step (4) to the end of step (5) was recorded as the wash/rinse time and the time from the beginning of step (5) to the end of step (5) was recorded as the rinse time. In almost all cases, the test panelists reported a relatively "sticky" or glutinous feel to the soap of Example 10.

The results showed that the wash/rinse/drying time and wash/rinse time were slightly higher for the soap of Example 10 than for the soap without phospholipids additive, on the order of 5% or so; however, the effect on rinse time was dramatic. Results appear in Table 7:

TABLE 7

Rinse Time Results
Rinse Time (seconds)

| Formulation A | Example 10 |
|---|---|
| 8.28 | 9.97 |
| 8.44 | 12.28 |
| 16.29 | 23.53 |
| 5.6 | 8.16 |
| 17.12 | 20.65 |
| 13.79 | 13.78 |
| 3.75 | 7.62 |
| 8.31 | 15.25 |
| 16.97 | 25.22 |
| 16.56 | 18.53 |
| 9.85 | 16.56 |
| 10.09 | 11.12 |
| 7.31 | 8.19 |
| 9 | 10.94 |
| 8.66 | 10.62 |
| 7.97 | 7.78 |
| 8.2 | 9.09 |
| 6.78 | 10.81 |
| 12.97 | 10 |
| AVG | AVG |
| 10.31 | 13.16 |
| % increase | 27.64 |

In Table 7 it is seen that the soap with phospholipid induced an average increase in rinse time of over 27% over all of the testing. Closer examination of the results suggests that other factors, perhaps random, had an impact on panelist behavior; for example, Table 8 shows that when Formulation A was tested first, rinse times were longer than when sample A was tested second, a result which appears anomalous.

TABLE 8

Comparison of Rinse Times and Order of Testing
Rinse Time

| A then 10 | | 10 then A | |
|---|---|---|---|
| A | 10 | 10 | A |
| 8.28 | 9.97 | 12.28 | 8.44 |
| 16.29 | 23.53 | 8.16 | 5.6 |
| 17.12 | 20.65 | 13.78 | 13.79 |
| 3.75 | 7.62 | 15.25 | 8.31 |
| 16.97 | 25.22 | 18.53 | 16.56 |
| 9.85 | 16.56 | 8.19 | 7.31 |
| 10.09 | 11.12 | 10.62 | 8.66 |
| 9 | 10.94 | 9.09 | 8.2 |
| 7.97 | 7.78 | 10 | 12.97 |
| 6.78 | 10.81 | | |
| AVG | AVG | AVG | AVG |
| 10.61 | 14.42 | 11.77 | 9.98 |
| % increase | 35.91 | 17.88 | % increase |

While the invention has been illustrated in connection with several examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. An antimicrobial liquid hand cleanser composition consisting essentially of:
   (a) water;
   (b) a primary hand cleanser surfactant composition comprising at least two anionic surfactants;
   (c) a biocide selected from the group consisting of halogenated aromatics, and phenolics; and
   (d) a glutinous surfactant component selected from the group consisting of: cocamidopropyl PG-dimonium chloride phosphate; dimer dilinoleamido-propyl PG-dimonium chloride phosphate; sodiumgrapeseedamidopropyl PG-dimonium chloride phosphate; sodium olivamidopropyl PG-dimonium chloride phosphate; linoleamidopropyl PG-dimonium chloride phosphate; PEG-8 dimethicone sunfloweramidopropyl PG-dimonium complex; sunfloweramidopropyl phosphate PG-dimonium chloride and mixtures thereof, wherein the surfactant has a relative contact angle value with water of at least about +10° with respect to the primary hand cleanser surfactant composition, the glutinous surfactant being present in an amount effective to alter the tactile properties of the primary hand cleanser surfactant composition, and wherein the glutinous surfactant component is present in an amount of more than 3% up to about 7% based on the total weight of the composition; and the composition is further characterized in that the relative amounts of glutinous surfactant and primary hand cleanser surfactant are such that the glutinous surfactant is present in an amount of less than about 20 weight % of the combined dry weight of the glutinous surfactant and the primary hand cleanser surfactant.

2. The antimicrobial hand cleanser according to claim 1, wherein the glutinous surfactant component comprises cocamidopropyl PG-dimonium chloride phosphate.

3. The liquid hand cleanser according to claim 1, wherein the glutinous surfactant component comprises dimer dilinoleamidopropyl PG-dimonium chloride phosphate.

4. The liquid hand cleanser according to claim 1, wherein the glutinous surfactant component comprises sodiumgrapeseedamidopropyl PG-dimonium chloride phosphate.

5. The liquid hand cleanser according to claim 1, wherein the glutinous surfactant component comprises sodium olivamidopropyl PG-dimonium chloride phosphate.

6. The liquid hand cleanser according to claim 1, wherein the glutinous surfactant component comprises linoleamidopropyl PG-dimonium chloride phosphate.

7. The liquid hand cleanser according to claim 1, wherein the glutinous surfactant component comprises PEG-8 dimethicone sunfloweramidopropyl PG-dimonium complex.

8. The liquid hand cleanser according to claim 1, wherein the glutinous surfactant component comprises sunfloweramidopropyl phosphate PG-dimonium chloride.

9. The liquid hand cleanser according to claim 1, wherein the glutinous surfactant component has a relative contact angle value with water of at least about +20° with respect to the primary surfactant composition.

10. The liquid hand cleanser composition according to claim 1, wherein the primary surfactant composition further comprises at least one nonionic surfactant.

11. The liquid hand cleanser composition according to claim 1, wherein the biocide comprises a halogenated aromatic compound.

12. The liquid hand cleanser composition according to claim 11, wherein the halogenated aromatic compound is:

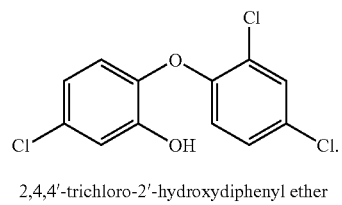

2,4,4'-trichloro-2'-hydroxydiphenyl ether

13. The liquid hand cleanser composition according to claim 1, further comprising a chelating agent.

14. The liquid hand cleanser composition according to claim 1, wherein the composition further comprises glycerine.

15. An antimicrobial liquid hand cleanser composition comprising:
   (a) water present in an amount of up to about 75% by weight;
   (b) a primary hand cleanser surfactant composition comprising at least two anionic surfactants;
   (c) a biocide selected from the group consisting of halogenated aromatics, and phenolics; and
   (d) a glutinous surfactant component selected from the group consisting of: cocamidopropyl PG-dimonium chloride phosphate; dimer dilinoleamido-propyl PG-dimonium chloride phosphate; sodiumgrapeseedamidopropyl PG-dimonium chloride phosphate; sodium olivamidopropyl PG-dimonium chloride phosphate; linoleamidopropyl PG-dimonium chloride phosphate; PEG-8 dimethicone sunfloweramidopropyl PG-dimonium complex; sunfloweramidopropyl phosphate PG-dimonium chloride and mixtures thereof, wherein the glutinous surfactant component is present in an amount of more than 3% by weight up to about 7% based on the total weight of the composition, the glutinous surfactant being operative to increase rinse time with respect to a like composition consisting of water and the primary surfactant composition.

16. The liquid hand cleanser composition according to claim 15, operative to increase rinse time at least 10% with respect to a like composition consisting of water and the primary surfactant composition.

17. The liquid hand cleanser composition according to claim 15, operative to increase rinse time at least 15% with respect to a like composition consisting of water and the primary surfactant composition.

18. The liquid hand cleanser composition according to claim 15, operative to increase rinse time at least 20% with respect to a like composition consisting of water and the primary surfactant composition.

19. A method of formulating a hand cleanser composition comprising preparing a mixture of:
   (a) water in an amount of up to about 75% by weight of the composition;
   (b) a primary hand cleanser surfactant composition comprising at least two anionic surfactants;
   (c) a biocide selected from the group consisting of halogenated aromatics, and phenolics; and
   (d) a glutinous surfactant component selected from the group consisting of: cocamidopropyl PG-dimonium chloride phosphate; dimer dilinoleamido-propyl PG-dimonium chloride phosphate; sodiumgrapeseedamidopropyl PG-dimonium chloride phosphate; sodium olivamidopropyl PG-dimonium chloride phosphate; linoleamidopropyl PG-dimonium chloride phosphate; PEG-8 dimethicone sunfloweramidopropyl PG-dimonium complex; sunfloweramidopropyl phosphate PG-dimonium chloride and mixtures thereof, wherein the glutinous surfactant is present in an amount of more than 3% by weight and up to about 7% by weight based on the weight of the composition including water and wherein the glutinous surfactant alters the tactile properties of the composition so as to lengthen hand cleansing times.

20. A liquid hand cleanser composition consisting essentially of:
   (a) water present in an amount of up to about 75% by weight;
   (b) a primary hand cleanser surfactant composition comprising at least two anionic surfactants;
   (c) a biocide selected from the group consisting of halogenated aromatics, and phenolics; and
   (d) a glutinous surfactant component selected from the group consisting of: cocamidopropyl PG-dimonium chloride phosphate; dimer dilinoleamido-propyl PG-dimonium chloride phosphate; sodiumgrapeseedamidopropyl PG-dimonium chloride phosphate; sodium olivamidopropyl PG-dimonium chloride phosphate; linoleamidopropyl PG-dimonium chloride phosphate; PEG-8 dimethicone sunfloweramidopropyl PG-dimonium complex; sunfloweramidopropyl phosphate PG-dimonium chloride and mixtures thereof, wherein the glutinous surfactant component is present in an amount of more than 3% by weight based on the total weight of the composition, the glutinous surfactant being operative to increase rinse time with respect to a like composition consisting of water and the primary surfactant composition.

21. The liquid hand cleanser composition according to claim 1, wherein the glutinous surfactant is present in an amount of at least 5% by weight based on the weight of the composition including water.

22. The liquid hand cleanser composition according to claim 15, wherein the glutinous surfactant is present in an amount of at least 5% by weight based on the weight of the composition including water.

23. The method according to claim 19, wherein the glutinous surfactant is present in an amount of at least 5% by weight based on the weight of the composition including water.

24. The liquid hand cleanser composition according to claim 20, wherein the glutinous surfactant is present in an amount of at least 5% by weight based on the weight of the composition including water.

* * * * *